(12) United States Patent
Oost et al.

(10) Patent No.: US 6,307,106 B1
(45) Date of Patent: *Oct. 23, 2001

(54) PROCESS FOR PREPARING UNSATURATED KETONES

(75) Inventors: Carsten Oost, Bad Dürkheim; Manfred Stroezel, Ilvesheim; Heinz Etzrodt, Neustadt; Dietmar Weller, Ludwigshafen; Gerd Kaibel, Lampertheim; Hagen Jaedicke, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/440,280

(22) Filed: Nov. 15, 1999

(30) Foreign Application Priority Data

Dec. 7, 1998 (DE) .............................. 198 53 908

(51) Int. Cl.⁷ .................................. C07C 45/00
(52) U.S. Cl. .................. 568/406; 568/346; 568/356; 568/383; 568/388; 568/391; 568/398
(58) Field of Search .................. 568/391, 346, 568/398, 356, 383, 388, 406

(56) References Cited

U.S. PATENT DOCUMENTS

| 3,860,655 | 1/1975 | Pommer et al. | 260/595 |
| 3,975,446 | 8/1976 | Kitagaki et al. | 260/593 R |
| 4,173,588 | 11/1979 | Pasedach et al. | 260/595 |
| 4,310,705 | * | 1/1982 | Nissen et al. | 568/391 |
| 5,874,635 | 2/1999 | Etzrodt et al. | 568/383 |

FOREIGN PATENT DOCUMENTS

| 1 286 018 | 1/1969 | (DE) . |
| 24 30 192 | 1/1975 | (DE) . |
| 26 52 863 | 5/1978 | (DE) . |
| 0 842 917 | 5/1998 | (EP) . |

* cited by examiner

Primary Examiner—Sreeni Padmanabhan
(74) Attorney, Agent, or Firm—Oblon, Spivak, McClelland, Maier & Neustadt, P.C.

(57) ABSTRACT

An improved process for preparing lower unsaturated ketones by reacting the corresponding α,β-unsaturated alcohols with alkyl acetoacetates in a Carroll reaction in the presence of from 0.1 to 5 mol %, based on the alkyl acetoacetate to be reacted, of an organic aluminum compound as catalyst with elimination and continuous removal by distillation of the alkanol eliminated during the reaction from the alkyl acetoacetate in a reactor system with a fitted fractionation column, wherein A an α,β-unsaturated alcohol which boils below 140° C. is introduced, in the absence of effective amounts of a solvent, together with the organic aluminum compound into the reaction vessel, B a reaction temperature which is as constant as possible between 170° C. and 250° C. is set under elevated pressure, C at this temperature, the alkyl acetoacetate is metered into the mixture, obtained in A, of the α,β-unsaturated alcohol and the organic aluminum compound, and D during the reaction the content of alkyl acetoacetate in the reaction mixture is set at a value which is as constant as possible between 0.1 and 10% by weight.

10 Claims, 2 Drawing Sheets

PROCESS FOR PREPARING UNSATURATED KETONES

The present invention relates to an improved process for preparing lower unsaturated ketones by reacting the corresponding α,β-unsaturated alcohols with alkyl acetoacetates in a Carroll reaction. The essential features of this reaction are already known, apart from the improvements according to the invention.

A reaction of this type between an unsaturated alcohol and an alkyl acetoacetate was described for the first time by Carroll in J. Chem. Soc. (London), 1940, pages 704 to 706. The same author reported one year later on the range of application and the mechanism of this reaction in J. Chem. Soc. (London), 1941, pages 507 to 511.

DE 1 068 696 discloses that it is possible to prepare 2-methyl-2-hepten-6-one by metering 2-methyl-3-buten-2-ol into a reaction mixture which has been preheated to 160 to 180° C. and consists of an alkyl acetoacetate, a mixture of an alkyl acetoacetate and an inert solvent or a mixture of 2-methyl-3-buten-2-ol, an alkyl acetoacetate and a solvent. The yields of 66%, based on the alkyl acetoacetate, achieved according to this patent are entirely inadequate for an industrial process.

Reaction of diketene, in place of the alkyl acetoacetate, with 2-methyl-3-buten-2-ol in the presence of aluminum triisopropoxide results in yields of 83% (cf. Advances in Organic Chemistry, Volume II, 1960, page 246). The disadvantage of this process is that the instability of diketene makes very complex apparatus necessary, for safety reasons, and therefore the capital and operating costs for an industrial system are high.

A number of other patents describing diverse variants of the Carroll reaction is known. Thus, in U.S. Pat. No. 2,795,617 (of 1957) or DE-B 1 053 498 (of 1959) or CH 342 947 (of 1959) it is stated that "although as a rule it is neither necessary nor desired, a solvent can be used in order to moderate the exothermic progress of the reaction". In the processes in these patents, the aluminum trialcoholate was added to the acetoacetate of the α,β-unsaturated alcohol, and the mixture was heated to reflux with vigorous stirring. Yields of up to 80% of theory were achieved in these cases. One disadvantage of this process is that the acetoacetate used as the starting compound must be prepared in a separate preceding stage.

U.S. Pat. No. 2,839,579 (of 1958) and DE 1 078 112 (of 1960) report that the reaction can be carried out in a solvent. The appropriate acetoacetate is prepared by condensing the appropriate unsaturated alcohol with diketene in a separate stage.

It is also stated in DE 1 068 696 that the presence of a solvent might be advantageous. High-boiling solvents with boiling points far above the reaction temperature are mentioned in all cases.

The disadvantages of these processes are that the yields stated in these patents are unsatisfactory for an industrial application and, in particular, that an additional process stage is necessary to prepare the acetoacetate of the α,β-unsaturated alcohol, which leads to additional costs. The proposed presence of a high-boiling solvent moreover generally results in negligible increases in yield and therefore leads only to a reduction in the space-time yield.

A process for preparing 2-methyl-2-hepten-6-one is described in DE-B 2 652 863 (of 1978). In this case, the alkyl acetocetate, 2-methyl-2-buten-3-ol and the catalyst are introduced into a reaction vessel with a fitted fractionation column, and then a mixture of the alkyl acetoacetate and 2-methyl-2-buten-3-ol is metered into this. During the reaction, the content of alkyl acetoacetate in the reaction mixture should not exceed 15% by weight, in order to avoid side reactions.

Czech Patent 216 360 (of 1979) recommends carrying out Carroll reactions in a mixture of the unsaturated ketone to be expected as reaction product, and the methyl or ethyl acetoacetate with addition of the unsaturated alcohol in an amount just sufficient to maintain the reaction. In this case, the carbon dioxide and a mixture of unreacted unsaturated alcohol and methanol or ethanol are distilled out of the reaction mixture, said mixture being continuously fractionated in an attached distillation column. The α,β-unsaturated alcohol, whose boiling point must be below 180° C., is then returned to the reaction. In this process, yields of about 80% of theory are achieved with reaction times of 8 hours. One disadvantage of the process is that additional capital and energy costs arise due to the additional distillation column. Moreover, the yields and reaction times in this process are unsatisfactory for a modern industrial process.

In addition, DE 2 928 944 (of 1979) describes the preparation of α,β-unsaturated ketones by a Carroll reaction in the presence of small amounts of a solvent whose boiling point is between that of the alkyl acetoacetate used and that of the alcohol to be eliminated therefrom. This solvent is referred to therein as "intermediate boiler". Possible inert intermediate boilers which are mentioned are alcohols, esters, ethers, halogenated hydrocarbons and aromatic hydrocarbons, preferably aliphatic ketones with 4 to 7 C atoms, having appropriate boiling points. The use of 2-methyl-3-buten-2-ol as reactive intermediate boiler is mentioned as a particularly advantageous embodiment, in which case an additional desired side reaction takes place between the latter and the alkyl acetoacetate to give 2-methyl-2-hepten-6-one as further required product. The advantages mentioned for the use of such an intermediate boiler are increased product yields (about 95% of theory based on the alcohol, and about 85% of theory based on the acetoacetate) and shorter reaction times (about 4–5 h) and thus high space-time yields. The reaction temperatures used in all the examples do not exceed 165° C.

However, the use of an intermediate boiler not only has advantages but also has the following disadvantages. Thus, for example, use of an inert intermediate boiler reduces the reactor volume available for the precursors, i.e. the space-time yields which can be achieved become inevitably smaller. In addition, for example, the presence of a reactive intermediate boiler such as 2-methyl-3-buten-2-ol results in enforced coupling of the production of different unsaturated ketones, which may be unwanted for a variety of reasons.

It is an object of the present invention to improve the reaction of relatively low-boiling α,β-unsaturated alcohols with alkyl acetoacetates in a Carroll reaction to give the corresponding unsaturated ketones in such a way that it can be carried out in the absence of a high-boiling solvent and without coupling to the preparation of other unsaturated ketones. It was moreover intended to achieve a product yield, based on the unsaturated alcohol and based on the alkyl acetoacetate, which is at least as good as, but if possible higher than, that in the syntheses described in the literature for separate preparation of the unsaturated ketones, with shorter reaction times. It was particularly intended to be able to prepare the ketone 2-methyl-2-hepten-6-one, which is in demand as fragrance and for preparing other fragrances, starting from 2-methyl-3-buten-2-ol without the prior art disadvantages and with higher selectivity and higher space-time yields.

We have found that this object is achieved by a process for preparing unsaturated ketones of the general formula I

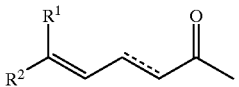
(I)

in which the dotted line can be an additional C—C bond, $R^1$ is an alkyl group with 1 or 2 C atoms, and $R^2$ is an alkyl group with 1 to 4 C atoms, by reacting α,β-unsaturated alcohols of the general formula II

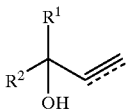
(II)

with alkyl acetoacetates of the general formula III

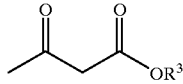
(III)

in which $R^3$ is an alkyl group with 1 to 4 C atoms, in the presence of from 0.1 to 5 mol %, based on the alkyl acetoacetate to be reacted, of an organic aluminum compound as catalyst with elimination and continuous removal by distillation of the alcohol which is eliminated from the alkyl acetoacetate during the reaction and has the general formula IV $R^3$—OH (IV)

in a reactor system with a fitted fractionation column, wherein

A an α,β-unsaturated alcohol which boils below 140° C., particularly 2-methyl-3-buten-2-ol, is introduced, in the absence of effective amounts of a solvent, together with the organic aluminum compound into the reaction vessel, B a reaction temperature which is as constant as possible between 170° C. and 250° C., preferably between 180° C. and 200° C., is set under elevated pressure, C at this temperature, the alkyl acetoacetate is metered into the mixture, obtained in A, of the α,β-unsaturated alcohol and the organic aluminum compound, and D during the reaction the content of alkyl acetoacetate in the reaction mixture is set at a value which is as constant as possible between 0.1 and 10% by weight, preferably between 1 and 3% by weight.

The selectivities (i.e. yields based on conversion, and only these are indicated in DE-B 26 52 683) for 2-methyl-2-hepten-6-one starting from 2-methyl-3-buten-2-ol achieved in this process are, within the limits available, comparable to those described in the Examples in DE-B 26 52 683.

The yields based on starting material, and the conversion based on methylbutenol, by contrast, are about 10% higher with the novel process than with the process disclosed in DE-B 26 52 683. This is a crucial advantage because this starting compound is considerably more costly than the alkyl acetoacetate. Another considerable advantage is that the higher conversions are achieved with identical selectivities despite a reaction time which is shorter by a factor of 3. The space-time yields are thus considerably higher with the novel process, which makes it possible to keep the capital costs lower.

It was very surprising that on use of the conditions according to the invention, i.e. in particular despite the absence of a solvent, application of higher pressures and use of reaction temperatures of from 175 to 220, preferably 180 to 200° C., scarcely any side reactions occur and thus excellent yields and space-time yields can be obtained. It is also surprising that it is possible, using the process according to the invention, even to react such low-boiling unsaturated alcohols as 2-methyl-3-buten-2-ol so advantageously to give the corresponding unsaturated ketone, 2-methyl-2-hepten-6-one, because it is expressly stated in DE-A-26 52 863 that it is impossible simply to introduce the alkyl acetoacetate into excess methylbutenol containing the aluminum compound at the reaction temperature because the 2-methyl-3-buten-2-ol has a boiling point of only 98° C. and the reaction does not start until 140° C. or above. Nor was it to be expected that, despite the use of higher pressures, the alkanol formed from the alkyl acetoacetate can be distilled out sufficiently well and rapidly to influence the reaction.

The product yields in the described process are thus about 95% of theory based on the alcohol used. The selectivity of the reaction, i.e. the yield based on the alcohol reacted, is in fact above 97% of theory, so that total yields of almost 100% can be achieved with the possibility of recycling the unreacted alcohol. The product yields based on the alkyl acetoacetate are between 90% and 95% when this reactant is completely decomposed. If complete decomposition of the alkyl acetoacetate is unnecessary, the selectivity based on the alcohol used can be increased by up to 2 percent if the acetoacetate is employed in excess (molar ratio of alcohol to acetoacetate between 0.7 and 0.9). However, in this case, losses of selectivity based on the acetoacetate must be expected, so that this procedure is worthwhile only with very costly alcohols. Recycling of unreacted reactants is otherwise worthwhile in every case.

The process according to the invention can in principle be applied to all known variants of the Carroll reaction in which the unsaturated alcohol employed boils below 140° C. However, the process is particularly important for synthesizing the fragrance 15 2-methyl-2-hepten-6-one starting from 2-methyl-3-buten-2-ol.

The reaction takes place in principle with any alkyl acetoacetates, but the methyl ester, the ethyl ester and the isopropyl ester will be preferred for both economic and technical reasons because the alkanols to be eliminated therefrom have a particularly low boiling point and thus can easily be removed from the reaction mixture.

Organic aluminum compounds suitable for the process according to the invention are compounds of the general formula

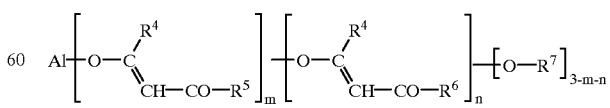
V in which $R^4$ are alkyl or alkoxy groups with 1 to 4 C atoms, preferably methyl or ethyl groups, $R^5$ and $R^6$ are alkyl or alkoxy groups with 1 to 5 C atoms, preferably methyl or a 2-butyl group, $R^7$ is an alkyl group with 1 to 4 C atoms, and m and n can assume values from 0 to 3, where n+m≦3, and aluminum triaryloxylates. Liquid aluminum compounds in which $R^5$ is a methyl radical and $R^6$ is a butyl radical, the total of n+m=3 and the n/m ratio is >0.3 are very particularly preferred.

The first-mentioned catalysts are therefore lower aluminum trialcoholates such as aluminum trimethoxide, triethoxide, triisopropoxide, tri-sec-butoxide and compounds formed on reaction of said aluminum trialcoholates with stoichiometric amounts of acetylacetonate, alkyl acetoacetate or alkyl malonate with elimination of alcohol and transesterification. Examples which may be mentioned are aluminum triacetoacetate, aluminum triacetylacetonate, aluminum monoacetoacetate diethoxide, aluminum monoacetoacetate diisopropoxide, aluminum diacetoacetate monoisopropoxide. The aluminum trialcoholates are preferably used, in particular aluminum triisopropoxide and aluminum tri-sec-butoxide. It is very particularly preferred to use the mixed aluminum triacetoacetate obtained by reacting aluminum sec-butoxide with methyl acetoacetate with elimination of 2-butanol and transesterification of the methoxy groups with the liberated 2-butanol, where the degree of transesterification is more than 30%.

The aluminum triaryloxylates referred to herein are the aluminum salts of aromatic hydroxyl compounds, such as aluminum triphenolate, aluminum tricresolates, aluminum trixylenolates, aluminum trinaphtholates, whose aryl radicals may also be substituted by lower alkyl or alkyloxy groups, i.e. alkyl or alkyloxy groups with 1 to 4 C atoms, hydroxyl groups or phenyl. It is particularly advantageous to use the relatively easily obtainable aluminum triphenolate.

The amount of aluminum compound is generally such that its concentration in the reaction mixture is not less than 0.05% by weight Al and, at the start of the reaction, does not exceed 6% by weight Al. Based on alkyl acetoacetate to be reacted, from 0.5 to 5 mol % of the aluminum compound are generally required. The amounts used of, for example, the aluminum triisopropoxide which is preferably used and the mixed aluminum triacetoacetate prepared from aluminum sec-butoxide and methyl acetoacetate as described above are, for example, about 1 to 3 mol % based on the alkyl acetoacetate to be reacted.

The selected amounts of reactants used in the process according to the invention are generally such that a molar ratio of unsaturated alcohol to alkyl acetoacetate of between 0.7 and 1.2, preferably between 0.95 and 1.05, results.

The pressure in the reaction vessel can be adjusted by injecting an inert gas and/or by collecting and injecting the carbon dioxide formed in the reaction, with the latter being preferred.

The reaction temperature is also essential for the success of the process and can be controlled in principle by suitable variation of the heat input and/or by variation of the rate of addition of the alkyl acetoacetate.

To facilitate the distillative removal of the alkanol formed in the reaction and to prevent delayed boiling it is advantageous to ensure adequate mixing of the reaction mixture in the reaction vessel. This can in principle be achieved by use of a powerful stirrer. However, it is particularly advantageous to achieve this by continuously pumping the reaction mixture through an external liquid circulation, by introducing the acetoacetate through a mixing nozzle into the reaction vessel or into the external liquid circulation or else by passing in a stream of inert gas or recycled carbon dioxide.

It is advantageous in the process according to the invention to remove the catalyst, together with high boilers formed as byproducts, from the reaction mixture and, after replacement of in each case 1 to 40% by weight, preferably between 20 and 30% by weight, of this mixture with fresh catalyst, to return it to the synthesis.

Particularly good selectivities are obtained when, after completion of the addition of the alkyl acetoacetate, the pressure in the reaction vessel, and thus the reaction temperature, is lowered for subsequent reaction, and, in addition, the removal of residual amounts of the alkanol of the formula IV from the reaction mixture is facilitated in this way.

The process according to the invention can be carried out very advantageously either batchwise or continuously.

BRIEF DESCRIPTION OF THE DRAWINGS

Batchwise procedure for the process according to the invention (cf.

Figure 1:
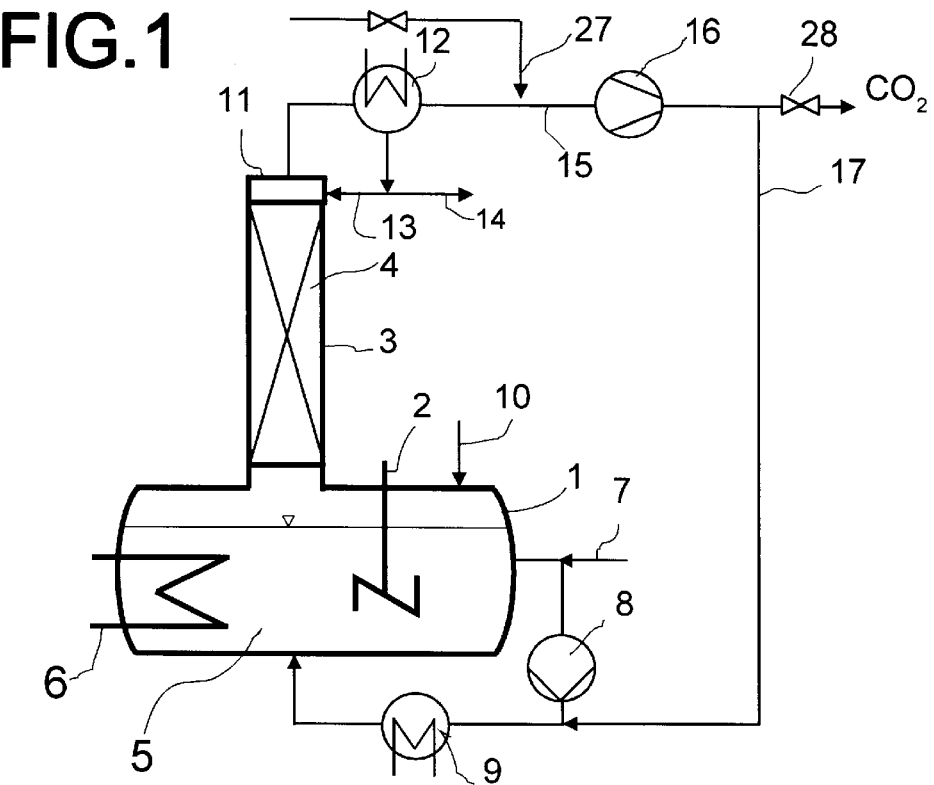
FIG. 1)

An example of a suitable reactor system for the batchwise reaction is a conventional heated distillation vessel (1) with stirrer (2) and fitted fractionation column (3) as depicted diagrammatically in FIG. 1. It is possible to use as fractionating column, for example, a column with about 2 to 40 theoretical plates. It is moreover possible to employ all types of column internals (4) such as ordered packings, column trays of various design or else random packings. The temperature in the reaction system is kept at the required level by variation of the heat input from the heat source (6) and, where appropriate, (9), by variation of the pressure, by feeding in heated inert gas where appropriate and/or by suitable variation of the metering of the alkyl acetoacetate.

It is expedient for the unsaturated alcohol of the formula II to be initially present together with the aluminum compound used as catalyst in the reaction vessel (1). Then, through a line (27), an inert gas such as nitrogen or carbon dioxide is injected and thus the required reaction pressure is set. It is likewise possible initially to increase the pressure only far enough for the boiling point of the alcohol to be high enough for the Carroll reaction to start, and then to build up to the required pressure in the system by means of the carbon dioxide formed during the reaction. As a rule, the initial boiling point of the reaction mixture should be at least 110° C.

The vessel contents (5) are then heated with a heating element (6) or with a heat exchanger (9) installed in the external circulation (7) with pump (8) with an infinite reflux ratio. After the required reaction temperature has been set, the alkyl acetoacetate of the formula (III) is metered through an inlet (10) into the vessel (1) or the external circulation (7) in such a way that a constant content of between 0.5 and 10% by weight, preferably between 1 and 3% by weight, of alkyl acetoacetate in the reaction solution (5) is reached. The pressure is set during the reaction with the aid of a pressure control device (28).

When the metering of the alkyl acetoacetate starts, the formation of alkanol of the general formula $R^3$—OH (IV) and carbon dioxide begins. The unsaturated alcohol of the formula (II) which is initially at the top of the column is displaced by the alkanol of the formula (IV) being liberated. The reflux ratio is set at a suitable value, and the reaction products are removed at the top (11) of the fitted column (3) and passed to the condenser (12). The condensed alkanol $R^3$—OH is partly recycled as return (13) to the column (3), and the other part (14) is taken off as distillate. The carbon dioxide (15) leaving the condenser can, for the stated reasons, be recycled with the aid of a compressor (16) through the line (17) into the reaction vessel (1). The metering of the alkyl acetoacetate through the inlet (10)

generally takes about 2 to 4 hours. If quantitative conversion of the alkyl acetoacetate is required, the reaction mixture should be kept at the reaction temperature for about 1 to 2 hours after the feeding in is complete. However, it is advantageous after completion of the metering in of the alkyl acetoacetate slowly to lower the pressure to atmospheric, in what is called the after-reaction phase, because this facilitates complete removal of the alkanol formed. The reaction temperature in the after-reaction phase should not exceed 180° C.

The progress of the reaction can be followed by measuring the carbon dioxide evolution in line (15) and/or on the basis of the amount of alcohol (14) eliminated from the alkyl acetoacetate. The concentration of alkyl acetoacetate in the reaction mixture (5) can be determined by gas chromatographic analysis.

Figure 2:
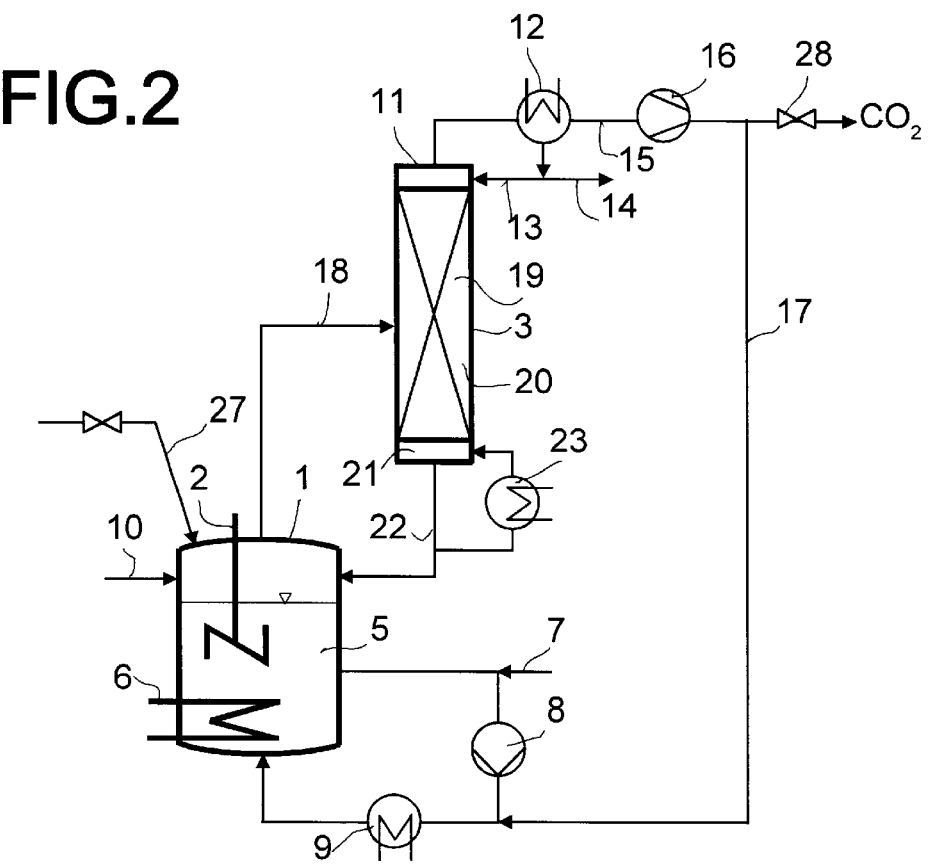

Alternative batchwise procedure as shown in FIG. 2.

A possible variant of the process described above is also to use as reactor a reaction vessel (1) with a nondirectly fitted fractionation column (3). In this case too, the reaction vessel is equipped where appropriate with a stirrer (2) and a heating element as heat source (6) and, where appropriate, with an external circulation (7) containing a pump (8) and, where appropriate, a heat source (9). The metering in of the alkyl acetoacetate takes place through the inlet (10). The vapors (18) emerging from the reaction vessel (1) are passed into a column (3) with concentration section (19) and stripping section (20). In this case, the carbon dioxide which is formed is removed, together with the alkanol produced, at the top (11) of the column and passed into the condenser (12). In analogy to the variant described above, the alcohol $R^3OH$ is condensed in the condenser (12) and partly recycled as return (13) to the column. It is likewise possible to compress the carbon dioxide with a compressor (16) and recycle it to the reaction vessel (1) through the line (17). The discharge containing unreacted reactants from the bottom (22) of the column (3) is recycled to the reaction vessel (1). The metering and reaction procedure correspond to the process described above.

Figure 3:
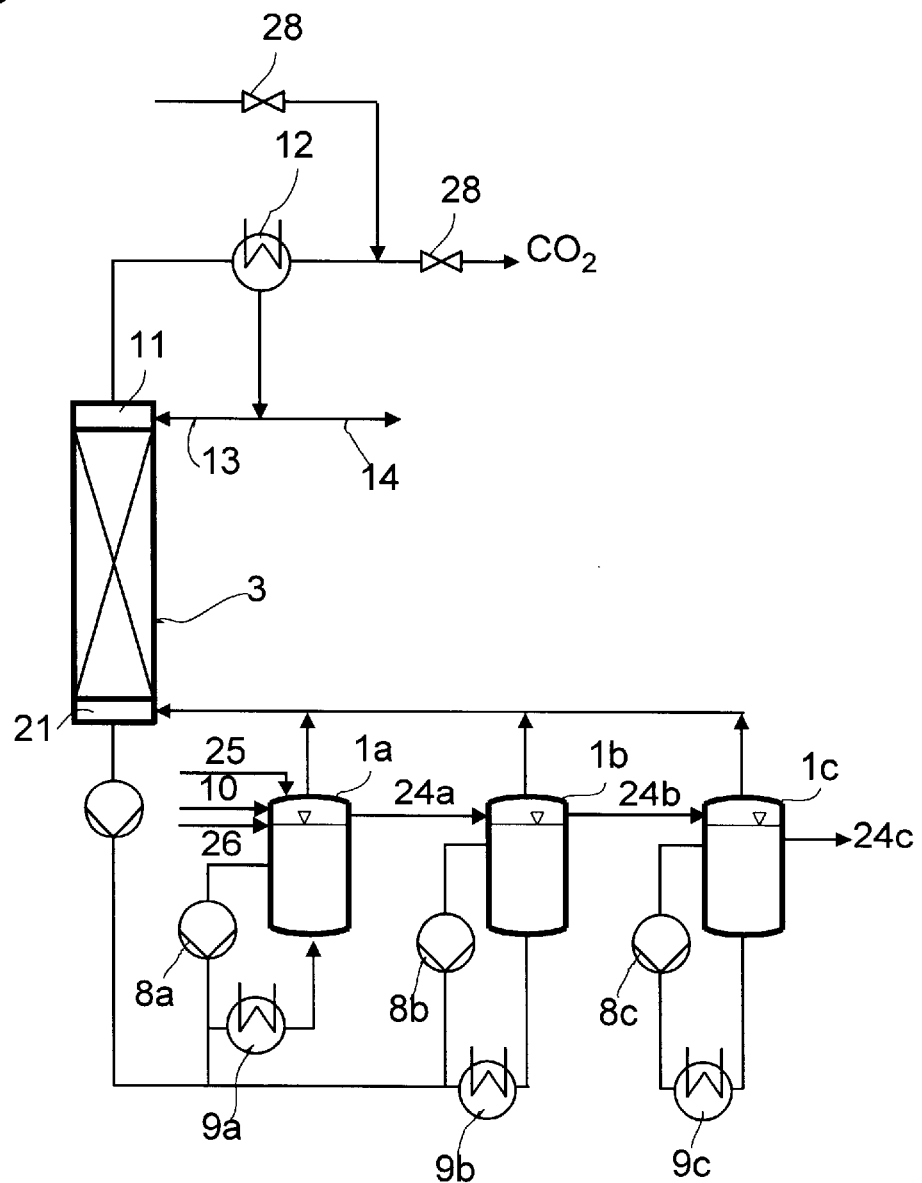

Continuous reaction (cf. FIG. 3)

When the reaction is carried out continuously, it is possible to use as reactor system, for example, a heated vessel cascade with 1 to 10, expediently 2 to 4, vessels. In this case, the individual vessels (e.g. 1a–1c) are each connected together by an overflow (e.g. 24a–24c). It is possible to fit a separate column to each vessel or else—as depicted in FIG. 3—to have only one column (3) for all the vessels.

The reactants are continuously introduced into the first vessel (1a), specifically the alcohols of the general formula II through the inlet (25), the alkyl acetoacetate through the inlet (10) and, where appropriate, the aluminum catalyst through the inlet (26). The setting of the reaction pressure required in the reaction vessel (1) and the column connected thereto using an external inert gas and/or the carbon dioxide formed is effected by a pressure control unit (28), advantageously in the manner depicted diagrammatically in FIG. 3. Maintenance of the required reaction temperature and the operation of the column (3) are essentially the same as for the batchwise procedure.

It is also possible for the catalyst used to be removed after completion of the reaction, for example with the aid of a thin film evaporator, and be recycled to the synthesis. It is advantageous in this connection for in each case 1 to 40% by weight of the residue of a batch, preferably between 20 and 30% by weight, to be replaced with a fresh catalyst and, at the same time, to remove the high boilers in this way.

It is possible with the aid of the process improved according to the invention to prepare numerous ketones, in particular 2-methyl-2-hepten-6-one, with virtually quantitative conversion in very high yields and space-time yields, and high purity.

EXAMPLE 1

Preparation of 2-methyl-2-hepten-6-one under 1.7 to 4 Bar

The test apparatus consisted of a heatable 2 liter stainless steel reaction flask which was equipped with a stirrer and fitted with a distillation column (length: 1 m, diameter: 25 mm). The column was packed with stainless steel wire coils (diameter: 5 mm). The reactants were metered in using a pump from the receivers which stood on a weighing device. The components methanol and $CO_2$ liberated during the reaction, and the volatile byproducts, isoprene and acetone, were removed through the column and condensed in a partial condenser. The condensate ran through a reflux divider into a receiver. The remaining off-gas stream was passed through a cold trap and then through a gas meter to measure the volume. The apparatus was equipped with a pressure control unit and designed for a system pressure of 10 bar. All the entering and emerging mass fluxes were measured and recorded continuously throughout the test to allow a time-dependent mass balance to be determined.

25.0 g (0.12 mol) of aluminum triisopropoxide, equivalent to 1.7 mol % based on the total amount of methyl acetoacetate (MAA), were mixed in a 200 ml stirred flask with 87.0 g (0.75 mol) of MAA and the mixture was heated to 140° C. The aluminum triisopropoxide dissolved in the MAA during this. Then 680.0 g of 2-methyl-3-buten-2-ol (MBE; 93% pure; 7.34 mol calculated for 100%) were introduced into a 2 liter stirred autoclave with fitted column and heated to 90° C. The catalyst solution at 140° C. was then mixed with the MBE at 90° C. in the stirred autoclave. Nitrogen was then injected from a gas cylinder and thus the reactor pressure was set at 1.7 bar (abs.). The reaction mixture was subsequently heated to 120° C. with a thermostat with an infinite reflux ratio. Starting at a temperature of 120° C., 724.3 g (6.24 mol) of MAA were metered linearly into the stirred autoclave over the course of 180 minutes (min). The reaction started when the metering began, so that $CO_2$ evolution started. This led to the reaction pressure building up to 4 bar (abs.) over the course of 30 min. The pressure was then maintained by the pressure control unit.

In the startup phase, mainly MBE distilled in the column and was returned with total reflux to the stirred autoclave. When the metering started, the MBE was displaced by the methanol liberated during the reaction. As soon as an overhead temperature of 104° C. (boiling point of methanol under 4 bar) was reached, the reflux ratio (RR) was set at 14. The resulting methanol was removed as distillate through the fitted column and $Co_2$ was removed with the aid of the pressure control unit so that the reactor pressure was kept at 4 bar. The temperature (T) of the reaction mixture rose during the reaction to 185° C. and was then controlled at 185° C. After 180 min, the MAA metering was terminated. The subsequent reaction started with termination of the MAA metering. The apparatus was slowly decompressed from 4 bar to atmospheric, during which the temperature (T) fell from 185° C. to 170° C. T was then controlled at 170° C. The subsequent reaction was terminated after 90 min. The catalyst and high boilers were removed by one-stage distillation, and the distillate was analyzed by gas chromatography.

2-Methyl-2-hepten-6-one was obtained with a selectivity of 92.1% of theory based on MBE reacted and 86.1% of theory based on MAA reacted, with an MBE conversion of 88.7% and a virtually quantitative MAA conversion.

EXAMPLE 2

Preparation of 2-methyl-2-hepten-6-one under 4 Bar 25.0 g (0.12 mol) of aluminum triisopropoxide, equivalent to 1.7 mol % based on the total amount of MAA, were mixed in a 200 ml stirred flask with 87.0 g (0.75 mol) of MAA and heated to 140° C. The aluminum triisopropoxide dissolved in the MAA during this. Then 672.0 g of MBE (94% pure; 7.33 mol calculated for 100%) were introduced into the 2 liter stirred autoclave with fitted column described in Example 1 and heated to 100° C. The catalyst solution at 140° C. was then mixed with MBE at 100° C. in the stirred autoclave. Nitrogen was subsequently injected from a gas cylinder and thus the reactor pressure was set at 4.0 bar absolute (abs.). The reaction mixture was then heated to 145° C. with a thermostat with an infinite reflux ratio, and 724.3 g (6.24 mol) of MAA were metered linearly into the stirred autoclave over the course of 180 min. The reaction started when the metering began, so that $CO_2$ evolution started. The pressure was maintained by the pressure control unit. As soon as an overhead temperature of 104° C. (boiling point of methanol under 4 bar) was reached, the reflux ratio RR was set at 15. The resulting methanol was removed as distillate through the heated column, and the $CO_2$ was removed with the aid of the pressure control unit so that the reactor pressure was kept at 4 bar. The T of the reaction mixture rose to 185° C. during the reaction and was then controlled at 185° C. After 180 min, the MAA metering was terminated. The subsequent reaction in which the apparatus was kept at 4 bar for 15 min started with the termination of the MAA metering. The pressure was slowly reduced from 4 bar to atmospheric, during which T fell from 185° C. to 170° C. The T was then controlled at 170° C. The subsequent reaction was terminated after 90 min. The catalyst and the high boilers were removed by a one-stage distillation, and the distillate was analyzed by gas chromatography.

The 2-methyl-2-hepten-6-one was obtained with a selectivity of 90.7% of theory based on MBE reacted, and a selectivity of 83% of theory based on MAA reacted, with an MBE conversion of 87% and a virtually quantitative MAA conversion.

EXAMPLE 3

Preparation of 2-methyl-2-hepten-6-one under 4 Bar with Recycling of the Catalyst A series of tests with recycling of the catalyst in 11 cycles was carried out in the apparatus described above in analogy to Example 1. This entailed the entire reaction mixture being worked up by a one-stage distillation after each test and, in each case, 25% by weight of the resulting residue being removed. Fresh catalyst was added, in the amount present in the removed material, to the remaining residue. The corresponding amount of fresh $Al(OiPr)_3$ was directly dissolved in the residue and employed as catalyst in the following test. With this procedure, a selectivity averaging 90% of theory based on MBE reacted, and a selectivity averaging 83% of theory based on MAA reacted, were achieved over 11 tests with an average MBE conversion of 88% and a virtually quantitative MAA conversion. No fall in the yields was observed even after ten recyclings.

We claim:

1. A process for preparing unsaturated ketones of the general formula I

(I)

in which the dotted line can be an additional C—C bond, $R^1$ is an alkyl group with 1 or 2 C atoms, and $R^2$ is an alkyl group with 1 to 4 C atoms, by reacting α,β-unsaturated alcohols of the general formula II

(II)

with alkyl acetoacetates of the general formula III

(III)

in which $R^3$ is an alkyl group with 1 to 4 C atoms, in the presence of from 0.1 to 5 mol %, based on the alkyl acetoacetate to be reacted, of an organic aluminum compound as catalyst with elimination and continuous removal by distillation of the alcohol which is eliminated from the alkyl acetoacetate during the reaction and has the general formula IV $$R^3—OH \qquad (IV)$$

in a reactor system with a fitted fractionation column, wherein

A an α,β-unsaturated alcohol which boils below 140° C. is introduced, in the absence of effective amounts of a solvent, together with the organic aluminum compound into the reaction vessel, B a reaction temperature which is as constant as possible between 170° C. and 250° C. is set under elevated pressure, C at this temperature, the alkyl acetoacetate is metered into the mixture, obtained in A, of the α,β-unsaturated alcohol and the organic aluminum compound, and D during the reaction the content of alkyl acetoacetate in the reaction mixture is set at a value which is as constant as possible between 0.1 and 10% by weight.

2. A process as claimed in claim 1, wherein the organic aluminum compound used is an aluminum compound of the general formula (V)

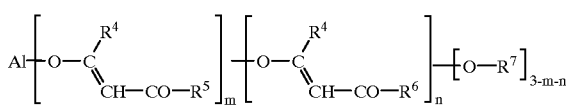
V in which $R^4$ are alkyl or alkoxy groups with 1 to 4 C atoms, $R^5$ and $R^6$ are alkyl or alkoxy groups with 1 to 5 C atoms, $R^7$ is an alkyl group with 1 to 4 C atoms, and m and n can assume values from 0 to 3, where $n+m \leq 3$, or an aluminum triaryloxylate.

3. A process as claimed in claim 1, wherein the amounts of the reactants employed are chosen to result in a molar ratio of alcohol to alkyl acetoacetate of between 0.95 and 1.05.

4. A process as claimed in claim 1, wherein 2-methyl-3-buten-2-ol is used as α,β-unsaturated alcohol of the general formula II which boils below 140° C. under normal conditions.

5. A process as claimed in claim 4, wherein the pressure in the reaction vessel is set by injecting an inert gas and/or by collecting and injecting the carbon dioxide formed in the reaction.

6. A process as claimed in claim 1, wherein the reaction temperature is controlled by suitable variation of the heat input and/or by variation of the rate of addition of alkyl acetoacetate.

7. A process as claimed in claim 1, wherein adequate mixing of the reaction mixture in the reaction vessel is ensured by use of a stirrer, by pumping the reaction mixture through an external liquid circulation, by introducing the alkyl acetoacetate through a mixing nozzle or else by passing in a stream of inert gas or recycled carbon dioxide, and thus the distillative removal of the alkanol of the general formula IV which is formed is facilitated.

8. A process as claimed in claim 1, wherein the catalyst is removed, together with high boilers formed as byproducts, from the reaction mixture and, after replacement of in each case 1 to 40% by weight with fresh catalyst, is returned to the synthesis.

9. A process as claimed in claim 1, wherein after completion of the addition of the alkyl acetoacetate the pressure in the reaction vessel is lowered for after-reaction.

10. A process as claimed in claim 2, wherein $R^4$ is independently methyl or ethyl, and $R^5$ and $R^6$ are independently methyl or a 2-butyl group.

* * * * *